US00PP29872P2

(12) United States Plant Patent
Barnes

(10) Patent No.: US PP29,872 P2
(45) Date of Patent: Nov. 20, 2018

(54) ***CALIBRACHOA* PLANT NAMED 'BBCAL76001'**

(50) Latin Name: ***Calibrachoa* sp.**
Varietal Denomination: BBCAL76001

(71) Applicant: Brent D. Barnes, Riverside, CA (US)

(72) Inventor: Brent D. Barnes, Riverside, CA (US)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 15/731,452

(22) Filed: Jun. 12, 2017

(51) Int. Cl.
*A01H 5/02* (2018.01)

(52) U.S. Cl.
USPC ..... Plt./413
CPC ..... *A01H 5/02* (2013.01)

(58) Field of Classification Search
USPC ..... Plt./413
CPC ..... A01H 5/02
See application file for complete search history.

(56) References Cited

PUBLICATIONS https://www.today.com/home/top-5-plants-sun-shade-drought-pest-control-2D80555531; Dec. 17, 2012; 1 page.*

* cited by examiner

*Primary Examiner* — Kent L Bell
(74) *Attorney, Agent, or Firm* — C. A. Whealy

(57) ABSTRACT

A new and distinct *Calibrachoa* plant named 'BBCAL76001', characterized by its compact, upright to outwardly spreading and mounding plant habit; moderately vigorous to vigorous growth habit; freely branching habit; dense and bushy appearance; freely flowering habit; purple-colored petals with a darker purple-colored central band encircling the yellow-colored throat; and good garden performance.

1 Drawing Sheet

Botanical designation: *Calibrachoa* sp.
Cultivar denomination: 'BBCAL76001'.

BACKGROUND OF THE INVENTION

The present invention relates to a new and distinct cultivar of *Calibrachoa* plant, botanically known as *Calibrachoa* sp. and hereinafter referred to by the name 'BBCAL76001'.

The new *Calibrachoa* plant is a product of a planned breeding program conducted by the Inventor in Bonsall, Calif. The objective of the breeding program is to create new uniform and freely-branching *Calibrachoa* plants with unique and attractive flower coloration and good garden performance.

The new *Calibrachoa* plant originated from a cross-pollination conducted by the Inventor in Bonsall, Calif. on Jul. 25, 2014 of *Calibrachoa* sp. 'Duealmidpu', disclosed in U.S. Plant Pat. No. 23,717, as the female, or seed, parent with a proprietary selection of *Calibrachoa* sp. identified as code number 14CB142-02, not patented, as the male, or pollen, parent. The new *Calibrachoa* plant was discovered and first selected by the Inventor as a single flowering plant within the progeny of the stated cross-pollination in a controlled greenhouse environment in Bonsall, Calif. on Jun. 9, 2015.

Asexual reproduction of the new *Calibrachoa* plant by vegetative terminal cuttings in a controlled greenhouse environment in Bonsall, Calif. since Jun. 9, 2015 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'BBCAL76001'. These characteristics in combination distinguish 'BBCAL76001' as a new and distinct *Calibrachoa* plant:

1. Compact, upright to outwardly spreading and mounding plant habit.
2. Moderately vigorous to vigorous growth habit.
3. Freely branching habit; dense and bushy appearance.
4. Freely flowering habit.
5. Purple-colored petals with a darker purple-colored central band encircling the yellow-colored throat.
6. Good garden performance.

The new *Calibrachoa* plant can be compared to plants of the female parent selection. Plants of the new *Calibrachoa* differ primarily from plants of the female parent, 'Duealmidpu', in plant habit as plants of the new *Calibrachoa* are more freely branching than plants of 'Duealmidpu'. In addition, plants of the new *Calibrachoa* are more tolerant to pathogens common to *Calibrachoa* plants than plants of 'Duealmidpu'.

The new *Calibrachoa* plant can be compared to plants of the male parent selection. Plants of the new *Calibrachoa* differ primarily from plants of the male parent selection in the following characteristics:

1. Plants of the new *Calibrachoa* are more mounding than and not as trailing as plants of the male parent selection.
2. Plants of the new *Calibrachoa* are more vigorous than plants of the male parent selection.

3. Plants of the new *Calibrachoa* have larger flowers than plants of the male parent selection.

Plants of the new *Calibrachoa* can be compared to plants of the *Calibrachoa* sp. 'USCALI99', disclosed in U.S. Plant Pat. No. 17,679. In side-by-side comparisons, plants of the new *Calibrachoa* differ primarily from plants of 'USCALI99' in the following characteristics:

1. Plants of the new *Calibrachoa* are more freely branching than plants of 'USCALI99'.
2. Plants of the new *Calibrachoa* have larger flowers than plants of 'USCALI99'.
3. Flowers of plants of the new *Calibrachoa* have greater resistance to fading than flowers of plants of 'USCALI99'.

Plants of the new *Calibrachoa* can also be compared to plants of the *Calibrachoa* sp. 'USCALI11', disclosed in U.S. Plant Pat. No. 14,968. In side-by-side comparisons, plants of the new *Calibrachoa* differ primarily from plants of 'USCALI11' in the following characteristics:

1. Plants of the new *Calibrachoa* are more freely branching than plants of 'USCALI11'.
2. Plants of the new *Calibrachoa* have larger flowers than plants of 'USCALI11'.
3. Plants of the new *Calibrachoa* and 'USCALI11' differ in flower color as plants of 'USCALI11' have light red purple-colored flowers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet is a side perspective view of a typical flowering plant of 'BBCAL76001' grown in a container.

The photograph at the top of the sheet is a close-up view of a typical flowering plant of 'BBCAL76001'.

DETAILED BOTANICAL DESCRIPTION

The aforementioned photographs and following observations and measurements describe plants grown during the spring in 11.5-cm containers in an acrylic-covered greenhouse in Carleton, Mich. and under cultural practices typical of commercial *Calibrachoa* production. During the production of the plants, day and night temperatures ranged from 18° C. to 27° C. Plants were six weeks from planting rooted cuttings when the photographs and description were taken. In the following description, color references are made to The Royal Horticultural Society Colour Chart, 2007 Edition, except where general terms of ordinary dictionary significance are used.

Botanical classification: *Calibrachoa* sp. 'BBCAL76001'.

Parentage:

*Female, or seed, parent.*—*Calibrachoa* sp. 'Duealmidpu', disclosed in U.S. Plant Pat. No. 23,717.

*Male, or pollen, parent*.—Proprietary selection of *Calibrachoa* sp. identified as code number 14CB142-02, not patented.

Propagation:

*Type*.—By vegetative terminal cuttings.

*Time to initiate roots, summer*.—About five to seven days at temperatures ranging from 17° C. to 29° C.

*Time to initiate roots, winter*.—About seven to ten days at temperatures ranging from 17° C. to 21° C.

*Time to produce a rooted plant, summer*.—About four to five weeks at temperatures ranging from 17° C. to 29° C.

*Time to produce a rooted plant, winter*.—About five to six weeks at temperatures ranging from 17° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, upright to outwardly spreading and mounding plant habit; moderately vigorous to vigorous growth habit; moderate growth rate; freely branching habit with about five primary lateral branches each with about two secondary branches; dense and bushy appearance.

*Plant height, soil level to top of foliar plane*.—About 8.5 cm.

*Plant height, soil level to top of floral plane*.—About 10 cm.

*Plant diameter*.—About 21 cm.

Lateral branch description:

*Length*.—About 10.2 cm.

*Diameter*.—About 1.5 mm.

*Internode length*.—About 5 mm to 8 mm.

*Strength*.—Strong.

*Aspect*.—Initially upright then outwardly spreading.

*Texture and luster*.—Minute pubescence; matte.

*Color, developing*.—Close to 145A.

*Color, developed*.—Close to 146D.

Leaf description:

*Arrangement*.—Before flowering, alternate; after flowering, opposite; leaves simple.

*Length*.—About 2.1 cm.

*Width*.—About 1 cm.

*Shape*.—Elliptical.

*Apex*.—Rounded to broadly acute.

*Base*.—Attenuate.

*Margin*.—Entire.

*Texture and luster, upper and lower surfaces*.—Minute pubescence; matte.

*Venation pattern*.—Pinnate; arcuate.

*Color*.—Developing leaves, upper and lower surfaces: Close to 146B. Fully expanded leaves, upper surface: Close to 137B; venation, close to 137C. Fully expanded leaves, lower surface: Close to 137C; venation, close to 146C.

*Petioles*.—Length: About 4 mm. Diameter: About 2 mm. Strength: Moderately strong. Texture and luster, upper and lower surfaces: Mostly smooth with scattered pubescence; matte. Color, upper and lower surfaces: Close to 146C.

Flower description:

*Flower type and flowering habit*.—Single salverform flowers arising from leaf axils; freely flowering habit with typically about 130 flowers and flower buds developing per plant; flowers face upright to outwardly.

*Fragrance*.—None detected.

*Natural flowering season*.—Plants of the new *Calibrachoa* begin flowering about six weeks after planting; plants flower continuously from the spring though the summer until frost.

*Flower longevity*.—Individual flowers last about four to five days on the plant; flowers persistent.

*Flower buds*.—Length: About 2 cm. Diameter: About 5 mm. Shape: Oblong, elongate. Texture and luster: Minute pubescence; matte. Color: Close to N200D tinted with close to N77D.

*Flower diameter*.—About 2.5 cm by 2.9 cm.

*Flower length* (*height*).—About 2.5 cm.

*Flower throat diameter*.—About 4 mm by 7 mm.

*Flower tube length*.—About 1.6 cm.

*Flower tube diameter*.—About 5 mm.

*Corolla*.—Arrangement: Five fused petals opening into a flared trumpet. Petal lobe length (from throat): About 1.2 cm. Petal lobe width: About 1.5 cm. Petal shape: Fan-shaped. Petal apex: Rounded. Petal margin: Entire. Petal texture and luster, upper surface: Smooth, glabrous, velvety; matte. Petal texture and luster, lower surface: Minute pubescence especially along the veins; matte. Throat texture and luster: Smooth, glabrous; slightly glossy. Tube texture and luster: Minute pubescence; matte. Color: Petal lobe, when opening, upper surface: Close to N79B to N79C. Petal lobe, when opening, lower surface: Close to N77D. Petal lobe, fully opened, upper surface: Slightly darker than 77A; band surrounding the throat, close to N79A; venation, close to N79A; color does not change with development. Petal lobe, fully opened, lower surface: Close to 79D; venation, close to 79A; color does not fade with development. Throat: Close to 7A; venation, close to 152B. Tube: Close to 145C; venation, close to 152C.

*Calyx*.—Arrangement: One star-shaped calyx tube with five sepals fused towards the base and arranged in a single whorl. Length: About 1.3 cm. Diameter: About 1.1 cm. Sepal length: About 9 mm. Sepal width: About 3 mm. Sepal shape: Lanceolate to narrowly elliptical. Sepal apex: Acute. Sepal margin: Entire. Sepal texture and luster, upper and lower surfaces: Minute pubescence; matte. Sepal color, upper and lower surfaces: Close to 146A.

*Peduncles*.—Length: About 1.1 cm. Diameter: About 1 mm. Angle: About 20° to 45° from stem axis. Strength: Moderately strong. Texture and luster: Minute pubescence; matte. Color: Close to 146C.

*Reproductive organs*.—Stamens: Quantity: Four per flower. Filament length: About 9 mm. Filament color: Close to 145C. Anther size: About 1 mm by 1 mm. Anther shape: Round. Anther color: Close to 8C. Pollen amount: Scarce. Pollen color: Close to 8A. Pistils: Quantity: One per flower. Pistil length: About 1 cm. Style length: About 8 mm. Style color: Close to 145C. Stigma diameter: About 1 mm. Stigma shape: Oval. Stigma color: Close to 146B. Ovary color: Close to 144A. Seeds and fruits: Seed and fruit development have not been observed on plants of the new *Calibrachoa* to date.

Garden performance: Plants of the new *Calibrachoa* have been observed to have good garden performance and tolerate wind, rain and to be suitable for USDA Hardiness Zones 9 to 11.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'BBCAL76001' as illustrated and described.

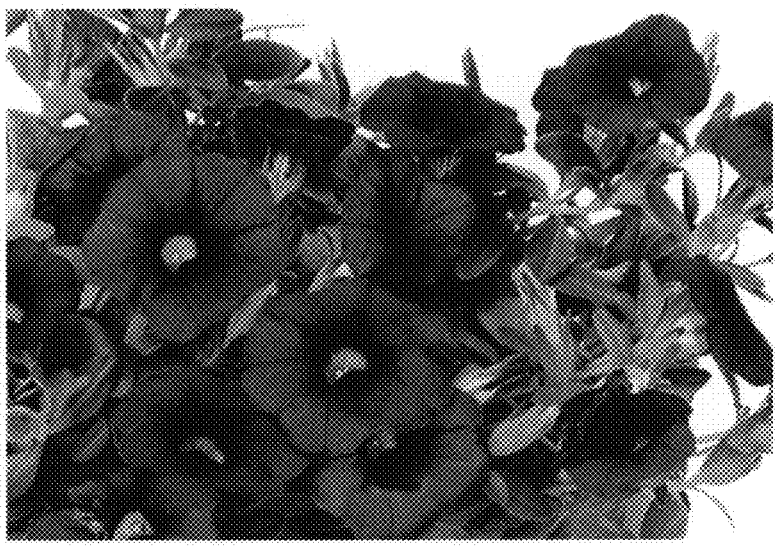
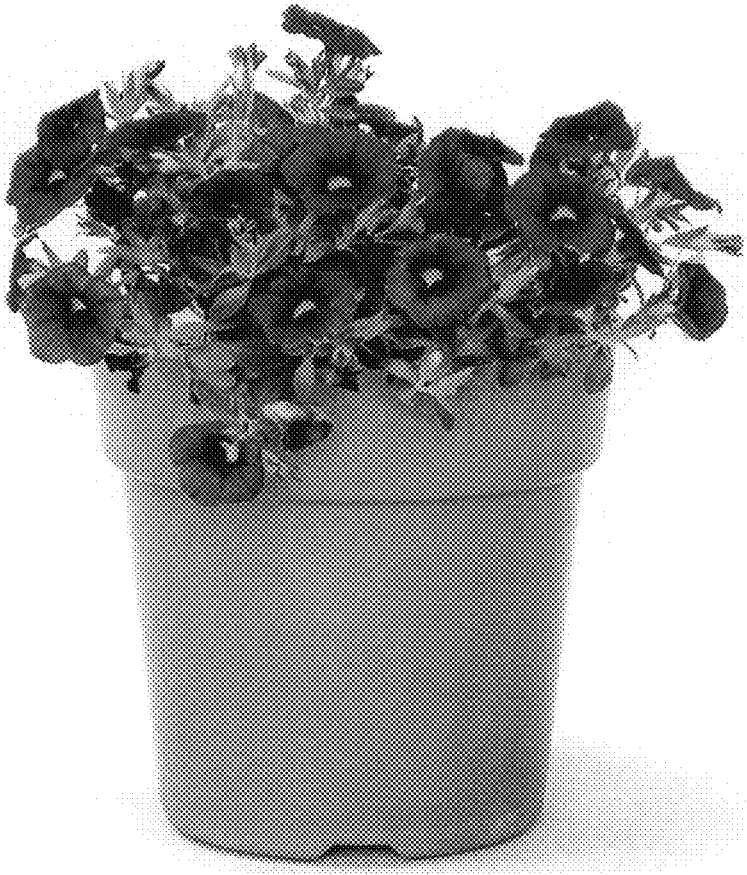

* * * * *